United States Patent [19]
Gisin et al.

[11] Patent Number: 5,349,431
[45] Date of Patent: Sep. 20, 1994

[54] APPARATUS FOR MEASURING CROSS-SECTIONAL DISTRIBUTION OF REFRACTIVE INDEX OF OPTICAL WAVEGUIDE

[75] Inventors: Nicolas Gisin, Geneva; Patrick Stamp; Rogerio Passy, both of Carouge, all of Switzerland; Nobuo Hori; Shigenori Nagano, both of Tokyo, Japan

[73] Assignee: Kabushiki Kaisha TOPCON, Tokyo, Japan

[21] Appl. No.: 85,200

[22] Filed: Jun. 30, 1993

[51] Int. Cl.$^5$ .................. G01N 21/41; G01N 21/43
[52] U.S. Cl. .................................. 356/73.1; 356/128
[58] Field of Search ............................ 356/73.1, 128

[56] References Cited

U.S. PATENT DOCUMENTS

| | | | |
|---|---|---|---|
| 5,278,628 | 1/1994 | Gisin et al. | 356/73.1 |
| 5,280,334 | 1/1994 | Gisin et al. | 356/73.1 |

Primary Examiner—Vincent P. McGraw
Attorney, Agent, or Firm—Nields & Lemack

[57] ABSTRACT

An optical waveguide portion is provided on one surface of a substrate portion. A luminous flux for measurement is caused to be incident on one end face of the optical waveguide substrate, and only leaking light having passed through the substrate portion is received. The cross-sectional distribution of the refractive index of the optical waveguide portion is measured from changes in the received quantity of light.

6 Claims, 7 Drawing Sheets

APPARATUS FOR MEASURING CROSS-SECTIONAL DISTRIBUTION OF REFRACTIVE INDEX OF OPTICAL WAVEGUIDE

BACKGROUND OF THE INVENTION

The present invention relates to an apparatus for measuring the cross-sectional distribution of the refractive index of an optical waveguide used for optical communication.

To measure the cross-sectional distribution of the refractive index of an optical waveguide, there is a refracted near field method (RNF method). This RNF method features high measuring accuracy and high resolution and is considered to be currently the most superior method of measuring the cross-sectional distribution of the refractive index on an optical waveguide.

Figure 9:
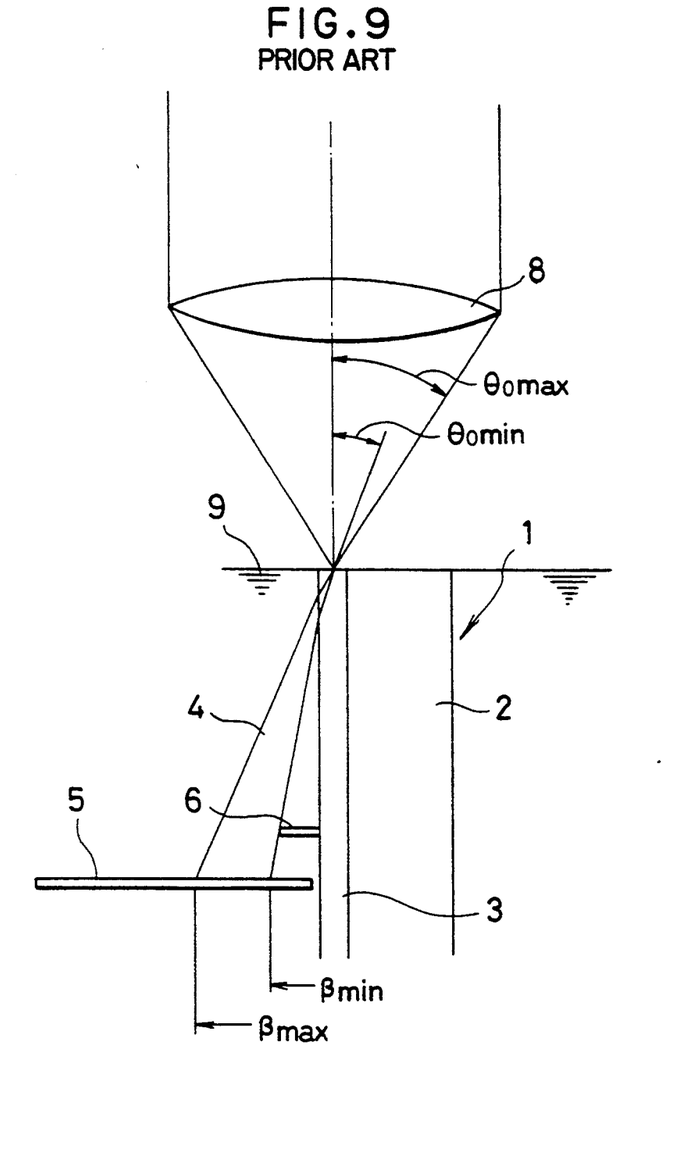
FIG. 9 is a drawing for explaining a conventional type example.

In the RNF method, as shown in FIG. 9, an optical waveguide substrate 1, which comprises a substrate portion 2 and an optical waveguide portion 3 formed on one surface of the substrate portion 2, is immersed in liquid 9 having a refractive index nL near the refractive index n(r) of the optical waveguide portion 3. In this state, a laser beam converged by an objective lens 8 is caused to be incident at an incident angle $\theta$ on an end face of the optical waveguide portion 3, and the light leaking from the optical waveguide portion 3 is detected to measure the refractive index of the optical waveguide portion 3.

When n(r) represents the refractive index of the optical waveguide portion 3 at the point of incidence of the laser beam, and n$\phi$ is the refractive index of air or liquid on the incidence side of the optical waveguide portion 3, the exit angle $\beta$ corresponding to the incident angle $\theta\phi$ is defined by the Snell's law and simply given as the following equation 1.

$$n^2(r) = n\phi^2 \cdot \sin^2\theta\phi + nL^2 \cdot \cos^2\beta \qquad (1)$$

Thus, by scanning the point of incidence of the laser beam in the thickness direction of the optical waveguide portion 3 or in the perpendicular direction to the thickness, the exit angle $\beta$ is changed according to the refractive index n(r) at each point. More specifically, the exit angle $\beta$ is reduced with increasing refractive index and increased with reducing refractive index.

Thus, it is possible to know the refractive index n(r) of the optical waveguide portion 3 by judging the state of leaking light.

The apparatus for measuring the cross-sectional distribution of the refractive index of an optical waveguide by the RNF method, is based on the above principle.

Referring to FIG. 9 again, a detector 5 for receiving light leaking from the optical waveguide portion 3 is provided sidewise of the optical waveguide substrate 1. Further, a semi-circular shielding plate 6 is provided such that it blocks a central portion of the leaking light flux 4. The detector 5 thus receives leaking light 4 having a half-doughnut-like sectional profile lacking a central portion. The light receiving quantity P is given as the following equation 2, where $\theta\phi$max represents the exit angle of the outermost light receiving point of the leaking light, and $\theta\phi$min represents exit angle of the innermost light receiving point shielded by the shielding plate 6.

$$P = \int_{\cos\theta\text{max}}^{\cos\theta\text{min}} I(\theta a) \cdot d(\cos\theta a) \qquad (2)$$

In the above equation, I($\theta\phi$) represents the angle dependency intensity distribution of the incident light. The light receiving surface of the detector 5 is made sufficiently large lest the leaking light 4 should get out of the light receiving surface. Thus, $\theta\phi$max in the equation 2 is determined by the numerical aperture (NA) of the objective lens and is given as the following equation 3.

$$n\theta\phi \cdot \sin\theta\phi\text{max} = NA \qquad (3)$$

The exit angle $\beta$max is changed, i.e., the outermost light receiving point of the leaking light is shifted, according to the refracting power of the optical waveguide portion 3, but the exit angle $\beta$min is determined absolutely by the positions of the edge of the shielding plate 6, and is not influenced by the refractive index of optical waveguide portion 3.

The incident angle $\theta\phi$min corresponding to the exit angle $\beta$min can be obtained by the equation 4, which is a rearrangement of the above equation 1.

$$n\phi^2 \cdot \sin^2\theta\phi\text{min} = n^2(r) - nL^2 \cdot \cos^2\beta\text{min} \qquad (4)$$

The incident angle $\theta\phi$min is an important factor in determining the refractive index of the optical waveguide portion 3. That is, the quantity of light that can be obtained by the equation 2 is changed according to the refractive index.

When it supposed that light receiving quantity at a driven point in the thickness direction of the optical waveguide portion 3 or in the perpendicular direction to the thickness is P(n(r)), this light receiving quantity P(n(r)) is given as the following equation 5.

$$P = (n(r)) \int_{\cos\theta\text{max}}^{\cos\theta\text{min}(n(r))} I(\theta a) \cdot d(\cos\theta a) \qquad (3)$$

Next, if the angle dependency I($\theta\phi$) of the incident light intensity has a Lambert distribution [I($\theta\phi$)=I$\phi$ cos$\theta\phi$], by scanning the laser spot position in the thickness direction of the optical waveguide portion or the perpendicular direction to the thickness and by measuring the change of light quantity $\Delta$P, the following equation 6 can be obtained from the above equation 5, and $\Delta$n(r) can be obtained from the equation 6.

$$\Delta P = a \cdot \Delta n(r) \qquad (6)$$

In this equation, the proportionality constant a is determined by the known refractive index $n_L$.

As the light source, a laser is usually used. In this case, the incident light intensity distribution I($\theta\phi$) is a Gauss distribution rather than a Lambert distribution, and change in the light quantity and change in the refractive index are not so simple as the equation 6. However, it is possible to obtain $\Delta$n(r) by correction by calculation.

In the above conventional type apparatus for measuring the cross-sectional refractive index distribution of an optical waveguide, the substrate portion of the optical waveguide is immersed in a liquid having a refractive index near, preferably higher than, that of the optical waveguide substrate portion in order to prevent total reflection of light in the optical waveguide portion and permit effective leaking of light incident on the optical waveguide portion to the outside thereof. That is, in the conventional type apparatus immersion liquid is indispensable.

In the case of an optical waveguide portion made of glass, the refractive index is about 1.5, and the immersion liquid can be comparatively readily selected. However, in many cases where an optical waveguide portion is formed by thermally diffusing Ti in a monocrystalline substrate of $LiNbO_3$, $LiTaO_3$, etc., the substrate portion has a refractive index of 2.0 or above.

With such optical waveguide substrate an immersion liquid having substantially the same refractive index is necessary. However, liquid with a refractive index of 2.0 or above is harmful to the human body. Further, depending on the material of the substrate, there may be no adequate immersion liquid even if the refractive index is low. Therefore, depending on the material of the optical waveguide portion the measurement is difficult or hazardous, or it is impossible.

The present invention has been intended in view of the above circumstances, and it seeks to permit the measurement of the refractive index distribution of optical waveguides without any immersion liquid.

The applicant has earlier proposed an another system for solving the problems pertaining to the invention in Japanese Patent Application 15481/1991.

DETAILED DESCRIPTION OF THE PREFERRED EMBODIMENT

In the following, the embodiment of the present invention will be described with reference to the drawings.

Figure 1:
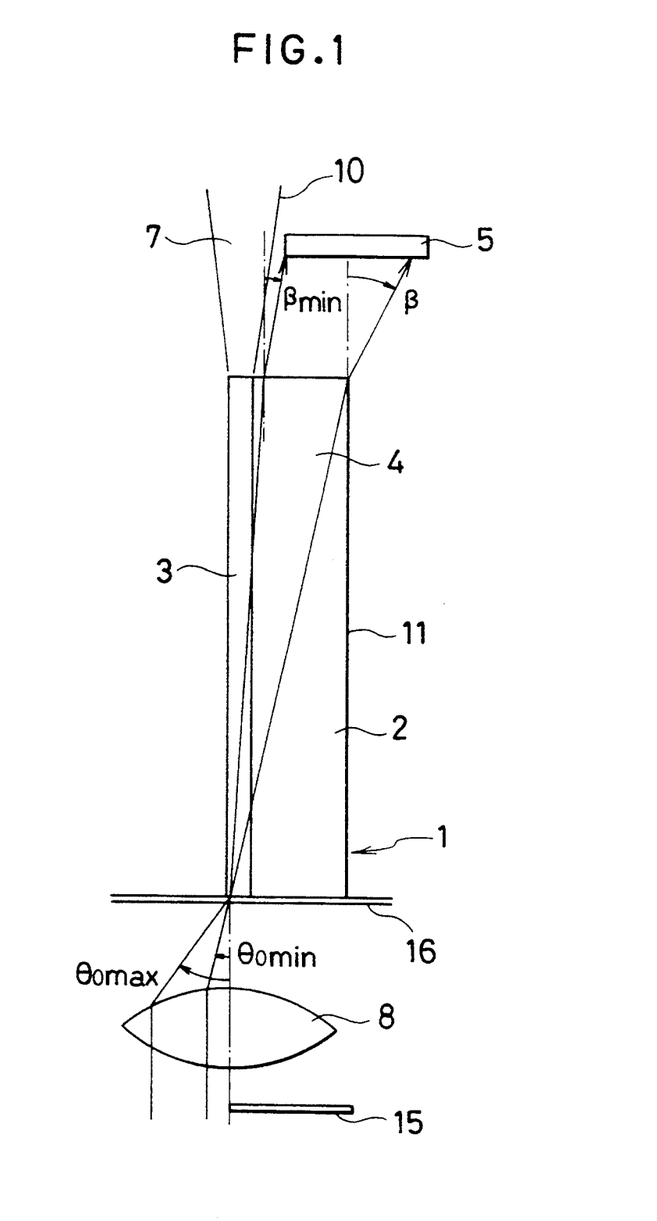
FIG. 1 is a schematic drawing showing an embodiment of the present invention.

Reference is made to FIG. 1, in which parts like those in FIG. 9 are designated by like reference numerals.

Figure 2:
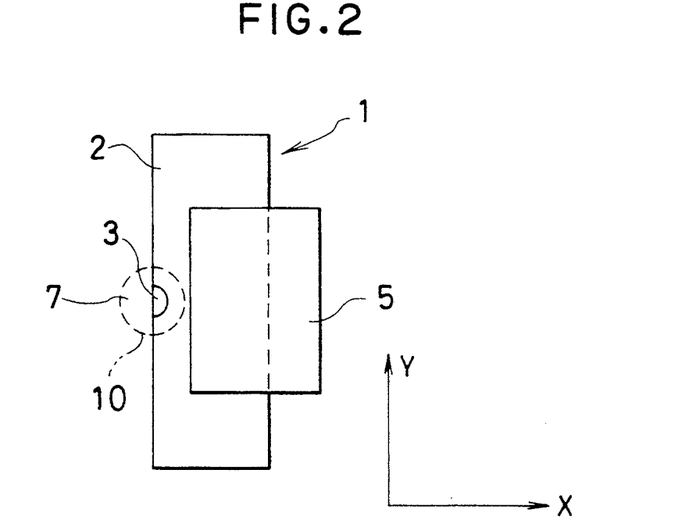
FIG. 2 is a drawing for explaining the shape and disposition of a detector in the same embodiment.

A detector 5 is disposed specially on the side opposite an objective lens 8 (i.e., above an optical waveguide substrate 1 in the Figure) such that it is parallel to the optical waveguide substrate 1. The detector 5 is disposed on the outer side of the maximum exit angle light 10 of the exit luminous flux 7 from the optical waveguide portion 3 (i.e., on the side away from the optical axis of the objective lens 8) lest it should receive luminous flux propagated through the optical waveguide portion. The detector 5 has a rectangular shape as shown in FIG. 2.

Designated at 15 in FIG. 1 is a semi-circular shielding diaphragm, and at 16 a glass cover. The optical waveguide portion 3 shown in FIG. 2 has a semi-circular cross-sectional shape, but may have a rectangular shape as well.

In this case, the detector 5 is not disposed sidewise of the optical waveguide substrate 1 as shown in FIG. 9, and thus the equation 1 is replaced with the following equation 7 .

$$n^2(r)=n\phi^2.\sin^2\theta\phi+n_S^2-n_1^2.\sin^2\beta \qquad (7)$$

Here $n_S$ represents the refractive index of the optical waveguide substrate portion 2, $n_1$ represents the refractive index of the medium, in which the detector 5 is disposed, and $\beta$ represents the exit angle from the optical waveguide substrate portion 2 to the medium.

Therefore, the incident angle $\theta_{\phi min}$ corresponding to the exit angle $\beta_{min}$ can be obtained by the equation 7 which is a rearrangement of the equation 8.

$$n_\phi^2. \sin^2\theta_{\phi min}=n^2(r)-n_S^2+n_1^2. \sin^2\beta_{min} \qquad (8)$$

Like the prior art RNF method, the incident angle $\theta_{\phi min}$ is an important factor in determining the refractive index of the optical waveguide portion 3. That is, the equation 5 holds as well according to the present invention.

However, the relation between the maximum exit angle $\beta max$ received by the detector 5 and the maximum incident angle $\theta_{\phi max}$ has to be considered. According to the conventional method of measurement as shown in FIG. 9, in which the detector 5 is disposed sidewise of the optical waveguide substrate 1, the maximum incident angle $\theta_{\phi max}$ of the luminous flux through the objective lens 8 and the maximum exit angle $\beta_{max}$ that can be received by the detector 5 correspond to each other absolutely. According to the invention, some considerations are needed in this respect.

That is, the status that can be assumed by the maximum incident angle $\theta_{\phi max}$ is changed slightly depending on the character of the back surface 11, on which the optical waveguide portion 3 is not formed, of the optical waveguide substrate 1.

For example, if the back surface 11 of the optical waveguide substrate 1 is polished like the surface, on which the optical waveguide portion 3 is formed, the detector 5 disposed in the close proximity of or in close contact with the optical waveguide substrate 1 can receive luminous flux covering almost all angle $\theta_\phi$ up to the maximum incident angle $\theta_{\phi max}$ through the objective lens 8.

Figure 8:
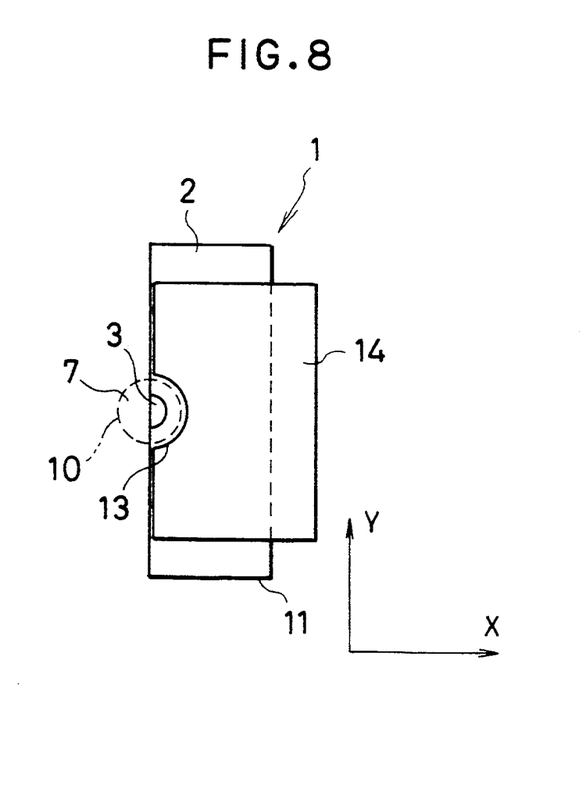
FIG. 8 is a drawing for explaining a further embodiment of the present invention.

If it is intended to obtain more continuous incident luminous flux, a detector 14 having a semi-circular notch 13 as shown in FIG. 8 may be used instead of the rectangular detector 5 as shown in FIG. 2. Or a light blocking member may be attached to the detector instead of a semi-circular notch 13.

Of course, the dimensions of the detectors 5 and 14 shown in the Y direction in FIG. 2 and FIG. 8 are sufficient to permit reception of the incident luminous flux with the maximum incident angle $\theta_{\phi max}$. Thus, the equations 3 and 5 hold as they are, and hence the equation 6 noted above also holds. This is so because of the facts that the refractive index of the optical waveguide substrate 1 is very high and that almost all the incident luminous flux through the objective lens 8 is reflected totally at the side surface of the optical waveguide substrate 1.

Figure 3:
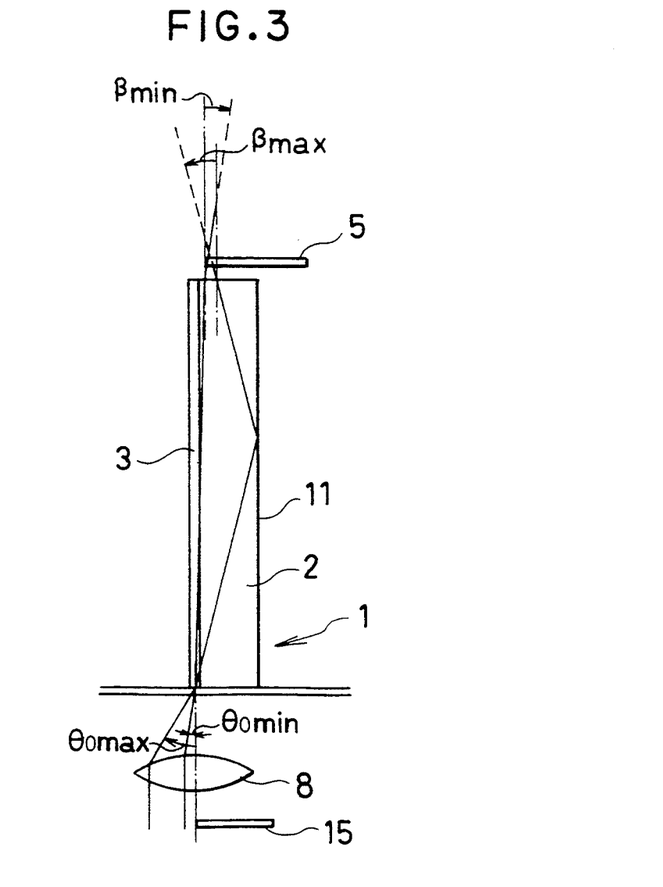
FIG. 3 is a drawing showing the relation between incident and exit angles in case where the back surface of an optical waveguide is a polished surface.

FIG. 3 shows only the total reflection by the back surface 11 of the optical waveguide substrate 1, but the same thing applies to the case of multiplex reflection by the front and back surfaces. Thus, where the back surface 11 of the optical waveguide substrate 1 without the optical waveguide is polished, the correspondence relation between the maximum exit angles $\beta_{max}$ and the maximum incident angle $\theta_{\phi max}$ is the same as in the conventional type example described before in connection with FIG. 9.

That is, the maximum incident angle $\theta_{\phi max}$ is determined by the effective numerical aperture (NA) of the objective lens 8, and thus the equation 3 holds. Further, as for the maximum exit angle $\beta_{max}$ the following equation 9 holds like the equation 8, and all the luminous flux in the exit angle range of $\beta_{min}$ to $\beta_{max}$ is received by the detector 5.

$$n_\phi^2 \cdot \sin^2\theta_{\phi max} = n^2(r) - n_S^2 + n_1^2 \cdot \sin^2\beta_{max} \qquad (9)$$

Now, a case, in which the back surface 11 of the optical waveguide substrate 1 is a sand-blasted surface (or diffusing surface), will be considered.

Figure 4:
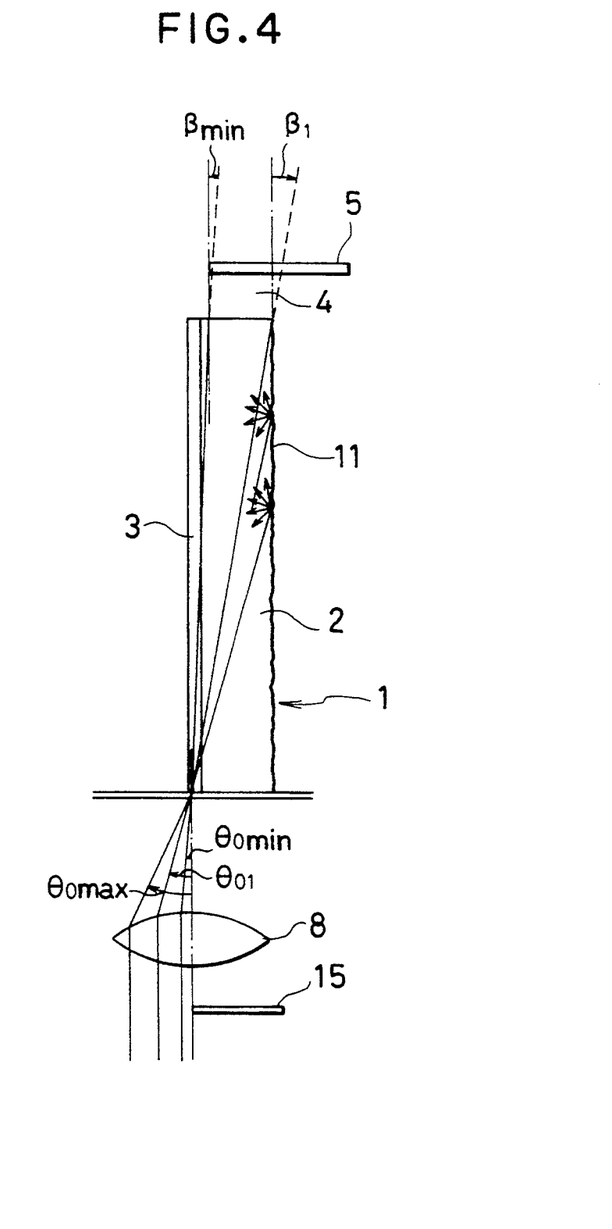
FIG. 4 is a drawing showing the relation between incident and exit angles in case where the back surface of an optical waveguide is a sand-blasted surface.
Figure 5A:
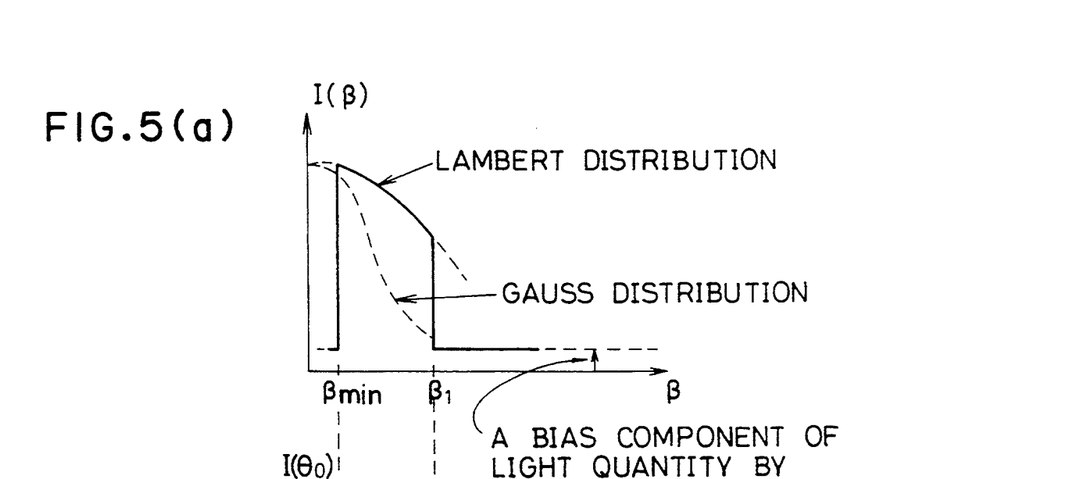
FIGS. 5(a) and 5(b) are graphs showing the angle dependency of light intensity distribution on incident angles $\theta\phi$ and exit angle $\beta$ for supplementary explanation in connection with FIG. 4.
Figure 5B:
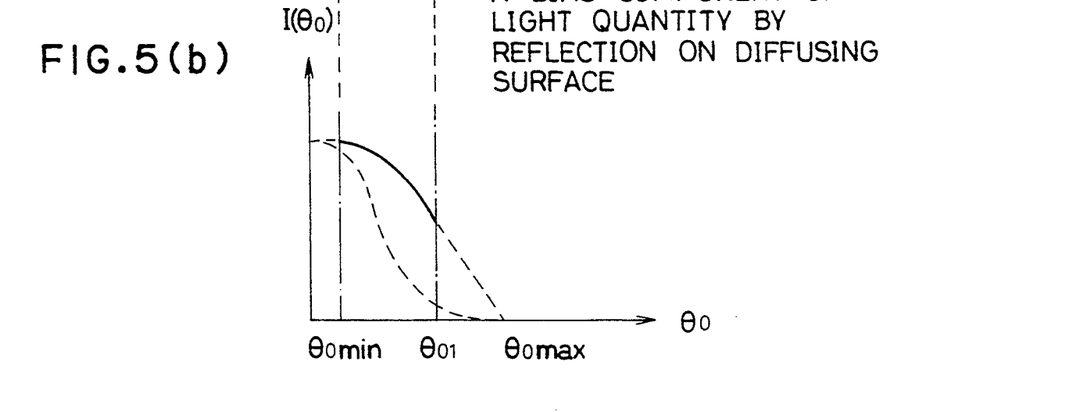

Reference is now be made to FIG. 4 and FIG. 5.

Of the luminous flux incident on the optical waveguide substrate 1 through the objective lens 8, the leaking light 4 from the optical waveguide portion 3 which directly reaches the detector 5 without being reflected by the front and back surfaces of the optical waveguide substrate 1 can be traced back for a range of the exit angle $\beta$ from the optical waveguide substrate 1 from $\beta_{min}$ to $\beta_1$ corresponding to the range $\theta_\phi$ of incident angle from $\theta_{\phi min}$ to $\theta_{\phi 1}$ through the objective lens 8, and can be determined absolutely.

Now, a large incident angle $\theta_\phi$ through the objective lens 8 such that the luminous flux is incident on the detector 5 after reflection by the back surface 11 of the optical waveguide substrate 1 will be considered.

In this case, since the back surface 11 of the optical waveguide substrate 1 is a sand-blasted surface, the luminous flux incident on the surface 11 is scattered, and therefore it can no longer be traced back when it reaches the detector 5.

However, although it is impossible to trace back the exit angle range $\theta_\phi$, it is considered that the luminous flux reflected by the back surface 11 has influence on the detector 5 as a bias component without angle dependence as shown in FIG. 5.

Thus, with the optical waveguide substrate 1 having a sand-blasted surface as its back surface 11, the lower limit $\cos\theta_{\phi max}$ of the range of integration of light energy received by the detector 5 as given by the equation 5 may be an adequate value if $\theta_{\phi max}$ is greater than $\theta_{\phi 1}$. This is so because what is needed as physical quantity when obtaining the cross-sectional distribution of the refractive index of the optical waveguide is not the total light quantity received by the detector 5 but the change in light quantity obtained by scanning the laser spot position in the thickness direction of the optical waveguide 3 or in the perpendicular direction to the thickness. In other words, when the back surface 11 of the optical waveguide substrate 1 is a sand-blasted surface, the equation 5 can be expressed as the following equation 10.

$$P = \int_{\cos 80 max}^{\cos 80 min(n(r))} I(\theta a) \cdot d(\cos\theta a) = \qquad (10)$$

$$\int_{\cos 80 max}^{\cos 801} I(\theta a) \cdot d(\cos\theta a) +$$

$$\int_{\cos 801}^{\cos 80 min(n(r))} I(\theta a) \cdot d(\cos\theta a) = \text{const} +$$

$$\cos 801 \cos 80 min(n(r)) I(\theta a) \cdot d(\cos\theta a)$$

Accurately, the second term of the equation 10, i.e., the lower limit $\cos\theta_{\phi 1}$ of the integral, is slightly influenced by changes in the cross-sectional refractive index distribution of the optical waveguide portion 3. However, as can be seen from FIG. 5(b), the incident luminous flux has angle-dependent intensity distribution $I(\theta_\phi)$. Thus, changes in the quantity of received light with changes in the cross-sectional refractive index distribution of the optical waveguide portion 3 with respect to $\theta_{\phi min}$ are predominant compared to changes in the quantity of light with changes in $\theta_{\phi 1}$.

In FIG. 5, the Lambert distribution is drawn by solid lines in the form of $I(\theta_\phi)$. With the usual laser, $I(\theta_\phi)$ rather provides Gauss distribution as shown by dashed lines. Thus, changes in the quantity of received light with changes in the cross-sectional refractive index distribution of the optical waveguide portion 3 with respect to $\theta_{\phi 1}$ are less noticeable.

Thus, changes in the quantity of light caused by the scanning can be expressed in the differential form of the equation 10. Thus, the equation 11 holds.

$$\Delta P = b \cdot \Delta n(r) \qquad (11)$$

It is thus verified that irrespective of whether the back surface 11 of the optical waveguide substrate 1 is a polished surface or a sand-blasted surface, the equation 6 and the equation 11 hold with respect to the lower limit of the integral in the equation 5 even by using $\cos\theta_{\phi max}$ in the conventional type example. Of course, the proportionality constants a and b expressed by the equation 6 and the equation 11 naturally have different values.

Now, a method of calculating the proportionality constants a and b, and obtaining the absolute value of the refractive index distribution will be described.

Now, an embodiment of the invention will be described with reference to FIG. 6.

Figure 6:
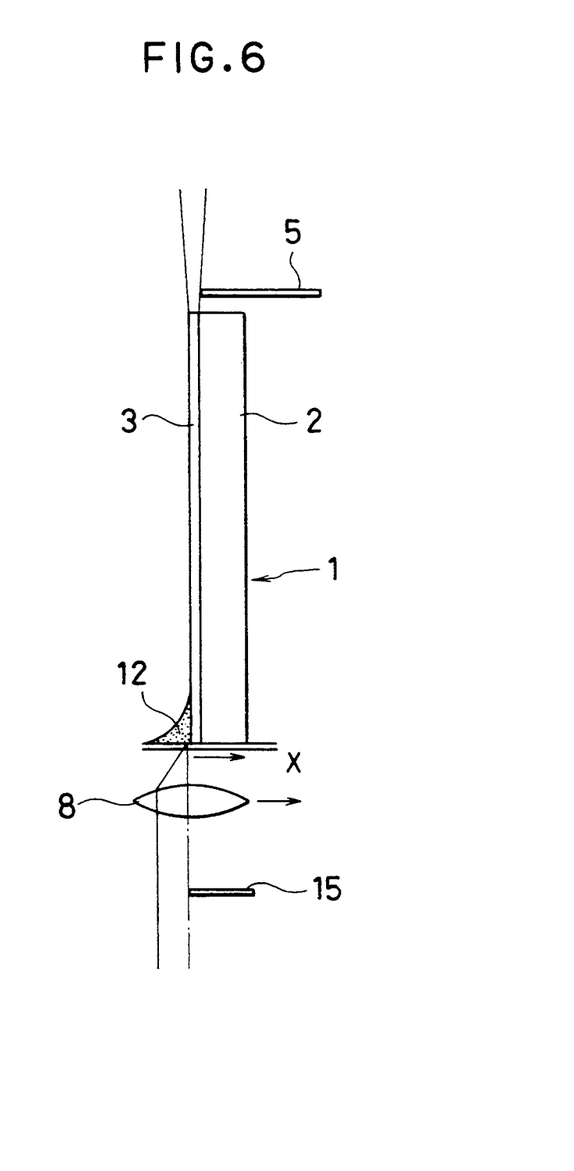
FIG. 6 is a drawing for explaining a different embodiment of the present invention.
Figure 7:
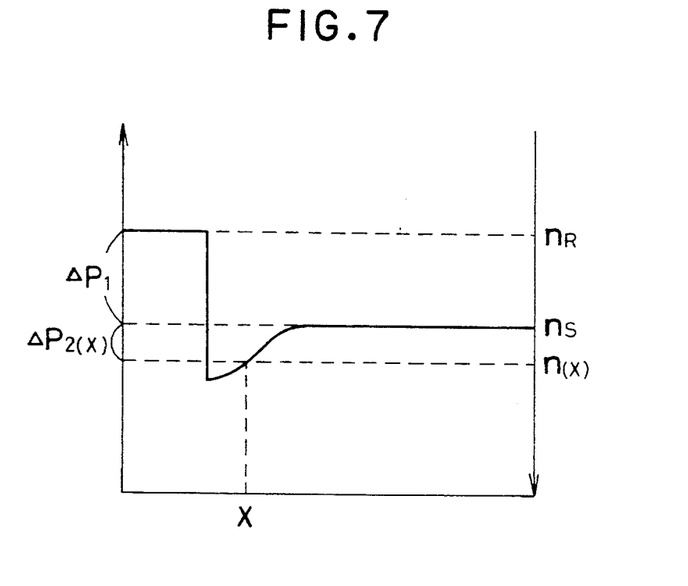
FIG. 7 is a graph showing change in the quantity of light for calculating proportionality constant and refractive index for supplement explanation in connection with FIG. 6.

Liquid 12 shown in FIG. 6 is a reference liquid having a known refractive index $n_R$ near the refractive index $n_S$ of optical waveguide substrate portion 2. It is provided as one drop on the surface of the optical waveguide substrate 1 with the optical waveguide portion 3. In this state, by scanning the laser spot position in the X direction shown in FIG. 6, changes in the light quantity as shown in FIG. 7 can be obtained.

Regarding the media of the refractive indexes $n_R$ and $n_S$ the change $\Delta P_1$ received by the detector 5 can be given, from the equation 6 and the equation 11, as the following equation 12.

$$\Delta P_1 = a(\text{or } b) \cdot \Delta n = a(\text{or } b) \cdot (n_S - n_R) \qquad (12)$$

Thus, the proportionality constant a or b can be determined as the following equation 13.

$$a \text{(or } b) = \frac{\Delta P_1}{nS - nR} \quad (13)$$

Further, since the following equation 14 holds for calculating the refractive index n(x) at an arbitrary optical waveguide cross-sectional surface position, the absolute value of the refractive index distribution n(r) (i.e., collective distribution with respect to the X and Y directions) of the optical waveguide 3 can be determined from the following equation 15.

$$(nS - nR) \cdot \Delta P_1 = \{n(X) - nS\} \cdot \Delta P_3(X) \quad (14)$$

$$n(X) - nS = \Delta P_2(X) \cdot \frac{nS - nR}{\Delta P_1}$$

$$\therefore n(X) = nS + \frac{\Delta P_2(X)}{a \text{(or } b)} \quad (15)$$

The refractive index $n_R$ is not limited to be lower than the refractive index $n_S$ of the optical waveguide substrate portion 2, but it may be higher as well. The closer $n_R$ to $n_S$, the proportionality constant can be determined more accurately.

The reference liquid 12 need not be used at all times in the measurement of the refractive index distribution of the optical waveguide 3, but it may be used only for the constant calibration.

As has been described in the foregoing, according to the present invention the refractive index distribution of the optical waveguide portion can be measured without immersion liquid having a refractive index substantially equal to that of the optical waveguide portion. Thus, it is possible to provide a very simple structure as the measuring apparatus. In addition, the measurement can be made in a ready operation. Further, since there is no need of using highly hazardous immersion liquid, the safety can be improved.

What we claim is:

1. An apparatus for measuring the cross-sectional distribution of the refractive index of an optical waveguide, comprising a projector system for causing a luminous flux for measurement to be incident on one end of an optical waveguide portion provided on one surface of a substrate portion and a light-receiving unit for receiving leaking light of said luminous flux for measurement from said optical waveguide portion, characterized in that said light-receiving unit is arranged at the other end of said optical waveguide portion such as to receive only leaking light having passed through said substrate portion, wherein the cross-sectional distribution of the refractive index of said optical waveguide portion is measured from changes in the amount of light incident on said light-receiving unit.

2. The apparatus for measuring the cross-sectional distribution of the refractive index of an optical waveguide according to claim 1, wherein the light-receiving unit and the substrate portion are in close contact with each other.

3. The apparatus for measuring the cross-sectional distribution of the refractive index of an optical waveguide according to claim 1, wherein a light-receiving unit is disposed on the outer side of the maximum exit angle light of the exit luminous flux from the optical waveguide portion.

4. The apparatus for measuring the cross-sectional distribution of the refractive index of an optical waveguide according to claim 1, wherein an unsensitising portion is provided at a light-receiving unit to prevent said light-receiving unit from receiving the luminous flux from the optical waveguide.

5. The apparatus for measuring the cross-sectional distribution of the refractive index of an optical waveguide according to claim 1, wherein the surface of the optical waveguide substrate is polished, at which the optical waveguide is not provided.

6. The apparatus for measuring the cross-sectional distribution of the refractive index of an optical waveguide according to claim 1, wherein the surface of the optical waveguide substrate is a diffusing surface, at which the optical waveguide is not provided.

* * * * *